(12) United States Patent
Stage

(10) Patent No.: US 6,415,785 B1
(45) Date of Patent: Jul. 9, 2002

(54) SELF CLOSING DIAPHRAGM TYPE VALVE WITH PRIMARY PERIPHERAL AND SECONDARY CENTRAL OPENINGS

(76) Inventor: Jack W. Stage, 100 Mt. Lyell Dr., San Rafael, CA (US) 94903

( * ) Notice: Subject to any disclaimer, the term of this patent is extended or adjusted under 35 U.S.C. 154(b) by 0 days.

(21) Appl. No.: 09/570,826

(22) Filed: May 15, 2000

Related U.S. Application Data

(60) Provisional application No. 60/135,563, filed on May 24, 1999.

(51) Int. Cl.[7] ............................................. A61M 15/00
(52) U.S. Cl. ............................ 128/200.23; 128/200.12
(58) Field of Search ..................... 128/200.11, 200.12, 128/200.14, 200.23, 200.24, 203.12, 203.13, 203.14, 203.15, 203.21, 205.24

(56) References Cited

U.S. PATENT DOCUMENTS

| 5,598,836 A | 2/1997 | Larson et al. ........... 128/200.23 |
| 5,904,139 A | 5/1999 | Hauser ................... 128/200.23 |

*Primary Examiner*—John G. Weiss
*Assistant Examiner*—Teena Mitchell

(57) ABSTRACT

A valve, shaped and sized for metered dose inhalers, consisting of a mount, a central body and top plate with peripheral air passages and central opening for medication delivery. A flexible elastic diaphragm closes the air passages and a central wiper seal on the diaphragm isolates the center opening from the air passageway. Pressure on the rim of the central opening of the diaphragm causes it to open the air passages timed with injection of medication through the central opening.

1 Claim, 2 Drawing Sheets

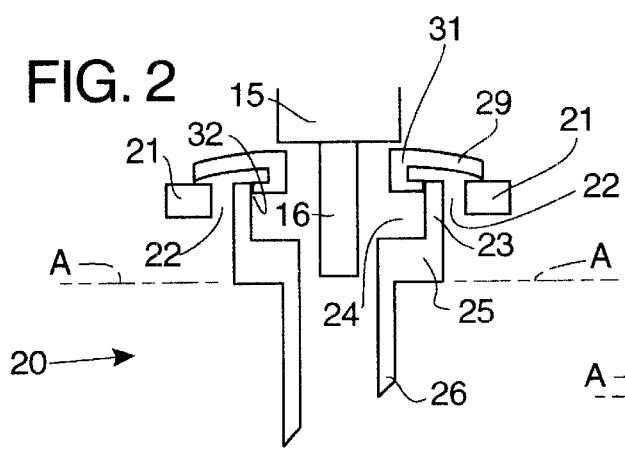
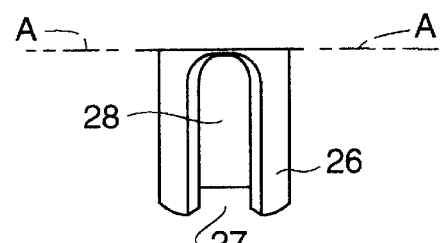
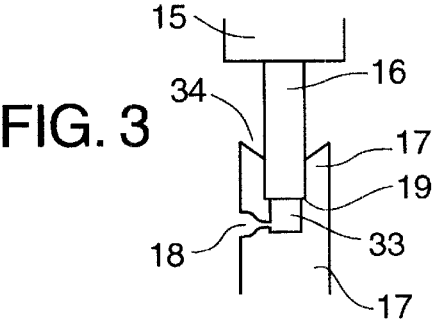
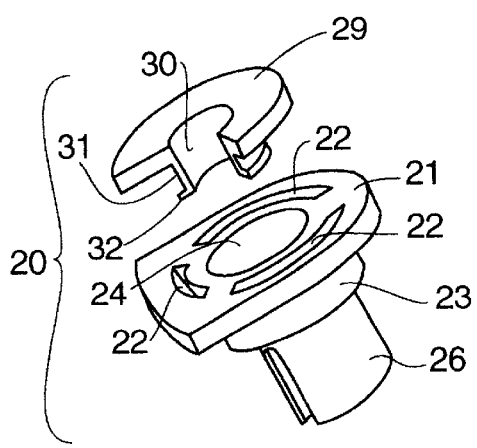
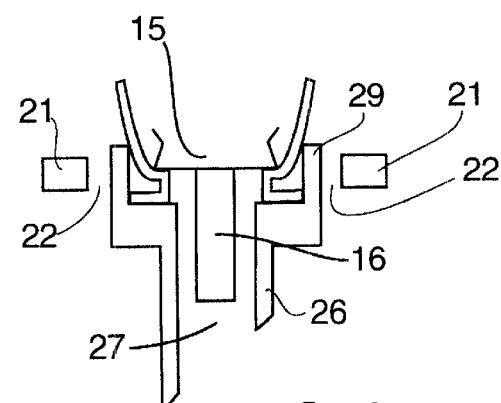

SELF CLOSING DIAPHRAGM TYPE VALVE WITH PRIMARY PERIPHERAL AND SECONDARY CENTRAL OPENINGS

CROSS-REFERENCES TO RELATED APPLICATIONS

This application is entitled to the benefit of Provisional Patent Application Serial No. 60/135,563 filed May 24, 1999.

BACKGROUND—FIELD OF INVENTION

This invention relates to metered dose inhalers with the specific intent for a reliable valve mechanism which will prevent inhalation of air until just prior to medication injection by the unit into the inhaled air stream without alteration of the medication spray in any way.

BACKGROUND—DESCRIPTION OF PRIOR ART

Millions of persons with asthma, chronic obstructive pulmonary disease, emphysema, and other pulmonary problems use metered dose inhalers for the administration of nebulized medications of various types into their lungs. Timing between the beginning of the inspiration of air to the injection of the nebulized medication is critical. Injection of medication to late deposits the medication in the mouth and throat. Injection to early carries the medication into the smallest air sacs of the lung, the alveoli, which in most cases is not desirable. The correct timing deposits the medication in the trachea, bronchi, and bronchioles. In all current metered dose inhaler units, there is an open breathing passage around a medication canister which must be depressed, against spring pressure, about 0.080 inches to begin medication injection, inspiration by the patient to begin at about 0.060 inches of movement. It is virtually impossible, even with training, to achieve perfect timing. As a result, pharmacists speculate that up to 50% of medication is wasted.

Devices such as described by Larson, et al, U.S. Pat. No. 5,598,836 allow air leakage at all times. Actually, huge quantities of air can be inhaled through minute openings before the medication spray which is not desired by pulmonary physiologists. The case is a complex mechanical device with no protection for the canister, a highly specialized device which would be expensive to manufacture and would require F.D.A. approval as a drug.

The mechanism of Hause, U.S. Pat. No. 5,904,139 is again a complex specialized case with vent holes sealed by a plunger seal which is held in place by either pressure of the internal spring mechanism of the medication canister, or by a separate spring which is placed above or below the canister which defeats the timing. The unit of Hause appears not to be reusable hence refill canisters, which are less costly than whole new units, could not be used. The unit would also appear to be non cleanable which is contrary to the desires of all manufacturers of metered dose inhalers and physicians prescribing them. It would also require F.D.A. approval as a drug.

Another device of a whole different nature, a spring loaded means which has to be cocked, with a button to press that triggers the opening of a flap valve and depresses the canister, is a highly specialized, expensive to construct means with many parts to fail, and this has not been a popular addition to the field.

No prior art has been able to utilize the actuator cases that are now in common usage.

SUMMARY

In accordance with the present invention, an insert valve comprises a tubular mounting means, with a lateral opening for medication spray, a cup like well holding a top plate with peripheral air passages and a central opening for medication delivery means, said top plate extending to the walls of the medication canister case and which by means of a flexible elastic diaphragm with a central opening and a wipe seal in the cup, prevents air passage until the medication canister is depressed, opening the air passages just prior to medication spray.

OBJECTS AND ADVANTAGES

Accordingly, several objects and advantages of my invention are an inexpensive, foolproof insert valve which can be molded to fit into any commonly used metered dose inhaler actuators currently in use with rare exception. It will effectively time inspiration to medication injection into the inhaled air stream and is self closing, not relying on the medication canisters internal retracting means. It will allow the medication canister to be removed for complete cleaning of the actuator, the removeable flexible diaphragm being easily reinserted. It may be used with more than one refill medication canister further saving expense. It does not allow leakage of air prior to activation, highly desired by pulmonary specialists, nor does it in any way interfere with medication dosage, plume velocity or shape, medication particle size, or air velocity around the medication spray. Another obvious advantage is that the metered dose inhaler is not changed in appearance or use. The user depresses the canister top as he or she has always done.

DRAWING FIGURES

FIG. 2 is a side view cross section of the valve in the resting or non activated mode.

FIG. 3 is a detail of the medication carrying tube inserted into a columnar stem like pedestal projection from the metered dose inhaler base with spray outlet and stop.

FIG. 4 is detail of the opening in the valve stem to allow medication to spray out.

FIG. 5 is an oblique exploded view of the valve with a cut away diaphragm.

FIG. 6 is an activated valve.

Figure 1:
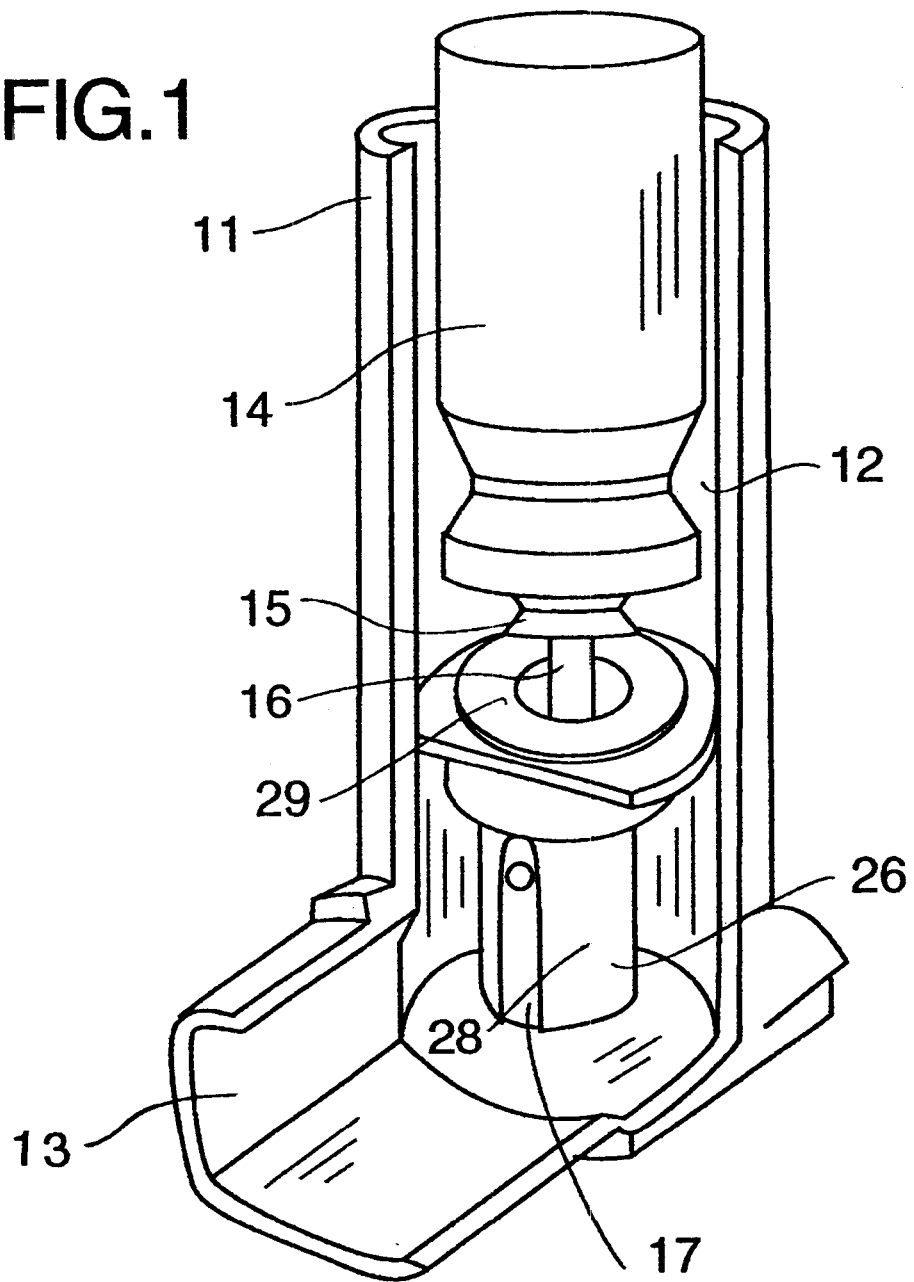
FIG. 1 is a cut away metered dose inhaler actuator with medication canister and insert valve in place. For clarity's sake the medication canister is shown higher above the diaphragm than in actual use.

REFERENCE NUMERALS IN DRAWINGS 11 case
12 canister chamber
13 mouthpiece
14 medication canister
15 canister base
16 medication tube from canister
17 pedestal from base
18 spray opening
19 stop
20 complete valve insert
21 top plate of valve
22 air passages
23 walls of cup-like cavity
24 cavity -continued 25 cavity base
26 tubular wall of support
27 hole through support
28 spray opening
29 flexible diaphragm
30 diaphragm central opening
31 tube part of diaphragm
32 wipe seal
33 medication cavity
34 pedestal tapered opening

DESCRIPTION—FIGURES 2,3,4,5,6—PREFERRED EMBODIMENT

A preferred embodiment of the present invention is illustrated in FIG. 2 (side view, resting mode), FIG. 6 (side view, activated mode), and FIG. 5 (oblique view). FIG. 4 shows a special feature of the tubular mount and FIG. 3 shows a medication carrying tube inserted into the pedestal base of the actuator. FIG. 1 is to orient the valve with the total metered dose inhaler actuator or case. The insert valve consists of three sections. A tubular base 26 ( FIGS. 2,4,5, and 6) with angled bottom to match the mouthpiece (FIG. 1) 13 angle, the internal diameter 27 of the tube to fit pedestal 17 has a cut out 28 (FIG. 4) to allow egress of medicine spray. The middle portion consists of a cup 24 with wall 23 and base 25 having a bottom central opening the same size as the internal diameter 27 of the tubular base 26. The upper portion is a plate 21 shaped and sized to fit the canister containing chamber 12 (FIG. 1) of the metered dose inhaler actuator or case. Circumferential air passages 22 around the cup wall 23 are to the periphery of top plate 21. A flexible, elastic diaphragm 29 of size to cover air passages 22 rests on top plate 21 with a central tube like downward extension 31 surrounding opening 30 and terminating in a bottom radial extension 32 of such size so as to form a wipe seal along cup 24 wall 23.

Advantages

From the description above, a number of advantages for this valve insert become evident:

(a) this insert valve is simple in construction and principle, therefore reasonable to produce.
(b) the metered dose inhaler actuator units now in use need no change in size, shape, or configuration.
(c) there are no loose parts to inhale, the diaphragm being trapped in place by the medication canister.
(d) it is not obvious, hence no visual cause for fear or anxiety by users because of a change.
(e) use of the metered dose inhaler is exactly the same procedure as it would be without the valve insert.
(f) in no way does it interfere with medication canister operation, medication dosage, spray velocity, spray plume size or shape, particle size of medication, or air velocity surrounding the medication spray.

Operation—FIGS. 1,2,3,6

A metered dose inhaler actuator unit (FIG. 1) consists of a plastic case 11, referred to as an actuator, with a medication canister chamber 12 contiguous with a mouthpiece 13. From the floor of the mouthpiece 13 arises a columnar pedestal 17 terminating at its upper end (FIG. 3) in a tapered opening 34 into which the medication carrying tube 16, passing through diaphragm opening 30, from the medication canister 14 base 15 is jam fitted, its lower most position being maintained by stop 19. The medication canister and base contain a spring loaded medication metering and dispensing system.

The insert valve 20 (FIG. 1) is a jam fit on the pedestal 17 and a jam fit against the walls of the canister chamber 12. This effectively creates two chambers in the metered dose inhaler actuator. The valve diaphragm seals the circumferentially arranged air passages 22, the wipe seal 32 sealing the cup 24 wall 23, the pedestal 17 sealing the valve tubular base opening 27, and the medication carrying tube 16 sealing the opening 34, the medication channel 33 and spray opening 18 in the pedestal 17.

When a patient places his mouth over the mouthpiece 13, he cannot inhale, all air passages being blocked. As he presses the canister 14 down, the canister base 15 (FIG. 6) contacts the inner circumference of the diaphragm 29 opening, moving it and wipe seal 32 down in cup 24, thereby lifting the outer circumference of the diaphragm 29 away from the valve top 21 and opening air passages 22. The patient is now able to inhale and with further downward movement of the canister, measured in thousandths of an inch and microseconds in time, the movement of the canister 14 and canister base 15 down on medication carrying tube 16 discharges medication down tube 16 into cavity 33 (FIG. 3) and out of spray hole 18. Continued pressure down on the canister maintains the air passages open to complete inspiration.

With release of pressure on the canister 14, its own internal spring mechanism retracts the canister 14 and base 15 on the discharge tube 16. The elastic diaphragm 29 and wipe seal 32 move upward returning to the resting position in which the air passages 22 are closed. The cycle may now be repeated.

The distance the canister and base move down on the discharge tube to discharge medication is minutely controlled so that the medication dose stays constant. This fixed discharge point is used to advantage in that the total height of the valve insert may be altered to allow timing, within reason, of the valve opening before medication spray so as to best suit patient needs.

Conclusions, Ramifications, and Scope

Accordingly, the reader will see that the self closing insert diaphragm valve with both peripheral and central openings for air flow and medication delivery, is the only device which will fit inside the currently used metered dose inhaler actuators, completely innocuous, and which can divide the air flow passage into two distinct sections responding to the normal use of the inhaler by timed opening of the air passage to precede medication injection into the air stream at the best time possible and without changing the usual use of the unit and without changing medication dosage, spray velocity, spray plume size or shape, medication particle size, and air stream velocity around the medication spray.

It is small, compact, easily and inexpensively produced, safe, and may be used with canister refills. It allows the metered dose inhaler unit to be taken apart, cleansed, with easy reinsertion of the elastic diaphragm with a finger tip so that the proper cleanliness may be maintained.

The timing of inhalation to injection of medication is difficult for almost everyone, especially the very young, and old so that 35–50% of most medication is wasted by not reaching the appropriate portions of the lung. This valve will reduce medication usage, waste, and subsequently the cost to patient and insurers while giving the best timing for inhaling medicine to allow the medication to reach the sites in the lung where it is needed. Special programs set up to try to teach people how to use these units will no longer be needed. The total financial saving should be substantial.

I claim:

1. An insertable breathing control valve adapted for metered dose inhalers consisting of:

a top plate, with or without peripheral seals, sized and shaped to so as to divide a metered dose inhaler into an upper and lower chamber, said top plate having a cylindrical cup like depression with a central bottom opening, an upper end and lower end between walls, said cup like depression being surrounded by circumferentially equispaced inlet air ports in said top plate;

said cylindrical cup like depression having at the lower end a contiguous hollow stem with an opening, the opening in said hollow stem being of a size to fit over a metered dose inhaler pedestal snug and essentially air tight and of length to hold said top plate in proper position so as to divide a metered dose inhaler into upper and lower chambers, said hollow stem having a side opening positioned so as to allow egress of medication spray;

a diaphragm of elastic material capable of returning to an original shape and position, sized to cover said circumferential equispaced inlet air ports, said diaphragm having a central stem like extension of a diameter to freely move in said circular cylindrical cup like depression of said top plate, said circular extension having a length to extend below a top surface of said top plate when said diaphragm is in a closed position, said central circular extension having at a terminal end a circumferential lateral extension so as to act as a wipe seal against the walls of said cyindrical cup like depression, both said diaphragm and said central stem like extension having a central opening of a sufficient diameter to allow unrestricted passage of a medication dispensing tube, yet be small enough so that an upper circumferential edge of said central opening may be engaged by a medication canister base or spacer placed over a medication dispensing tube for the purpose of depressing a central portion of said diaphragm, thus opening said air inlet ports, thereby allowing inspiration timed with delivery of medication.

\* \* \* \* \*